US010335580B2

(12) United States Patent
Chludzinski et al.

(10) Patent No.: US 10,335,580 B2
(45) Date of Patent: Jul. 2, 2019

(54) GUIDEWIRE WITH VARYING PROPERTIES

(71) Applicant: Abbott Cardiovascular Systems Inc., Santa Clara, CA (US)

(72) Inventors: Matthew James Chludzinski, Poway, CA (US); John Arthur Simpson, Carlsbad, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 601 days.

(21) Appl. No.: 15/007,013

(22) Filed: Jan. 26, 2016

(65) Prior Publication Data
US 2016/0136396 A1 May 19, 2016

Related U.S. Application Data

(63) Continuation-in-part of application No. 14/042,321, filed on Sep. 30, 2013.

(51) Int. Cl.
*B21C 1/00* (2006.01)
*B21J 7/14* (2006.01)
*A61M 25/09* (2006.01)
*B21F 45/00* (2006.01)

(52) U.S. Cl.
CPC ............ *A61M 25/09* (2013.01); *B21F 45/008* (2013.01); *A61M 2025/09108* (2013.01); *A61M 2025/09133* (2013.01); *A61M 2205/0216* (2013.01); *B21C 1/00* (2013.01); *B21J 7/145* (2013.01)

(58) Field of Classification Search
CPC ........ A61M 25/09; A61M 2025/09133; A61M 2025/09108; A61M 2205/0216; B21J 7/145; B21J 7/16; B21F 45/008
See application file for complete search history.

(56) References Cited

U.S. PATENT DOCUMENTS

| 2,199,602 | A | 5/1940 | Wright |
| 3,590,622 | A | 7/1971 | Elge et al. |
| 5,001,825 | A | 3/1991 | Halpern |
| 5,171,383 | A | 12/1992 | Sagaye et al. |

(Continued)

FOREIGN PATENT DOCUMENTS

| CN | 101674861 | 3/2010 |
| EP | 0395098 | 4/1990 |

(Continued)

OTHER PUBLICATIONS

P. Grupp; C Kienhoefer; 2003 Felss GmbH, Rotary Swaging Technology, 31 Pages.*

(Continued)

*Primary Examiner* — Gregory D Swiatocha
(74) *Attorney, Agent, or Firm* — Workman Nydegger

(57) ABSTRACT

A method of making a core metal element for a medical guidewire including providing a wire of nickel titanium alloy having a length that includes a proximal portion having a first diameter and a distal portion having a second diameter. The method further includes applying cold work to the distal portion and not applying cold work to the proximal portion, thereby imparting to the distal portion a third diameter that is smaller than the second diameter; and then applying a reducing process to the wire whereby the proximal portion is reduced to have a fourth diameter that is less than the first diameter.

9 Claims, 8 Drawing Sheets

(56) References Cited

U.S. PATENT DOCUMENTS

| | | | |
|---|---|---|---|
| 5,238,004 A | 8/1993 | Sahatjian et al. | |
| 5,365,943 A * | 11/1994 | Jansen | A61M 25/09 600/585 |
| 5,916,166 A | 6/1999 | Reiss et al. | |
| 6,019,736 A | 2/2000 | Avellanet et al. | |
| 6,042,553 A | 3/2000 | Solar et al. | |
| 6,068,623 A | 5/2000 | Zadno-Azizi et al. | |
| 6,168,571 B1 | 1/2001 | Solar et al. | |
| 6,190,332 B1 * | 2/2001 | Muni | A61M 25/09 600/585 |
| 6,375,629 B1 | 4/2002 | Muni et al. | |
| 6,450,975 B1 | 9/2002 | Brennan et al. | |
| 6,647,755 B2 * | 11/2003 | Rabiner | A61B 17/22012 72/276 |
| 6,736,843 B1 | 5/2004 | Fariabi | |
| 6,918,882 B2 | 7/2005 | Skujins et al. | |
| 7,998,090 B2 | 8/2011 | Simpson et al. | |
| 8,100,837 B1 | 1/2012 | Cornish et al. | |
| 8,454,537 B2 | 6/2013 | Simpson et al. | |
| 8,500,658 B2 | 8/2013 | Boyle et al. | |
| 8,679,035 B2 | 3/2014 | Boyle et al. | |
| 8,721,564 B2 | 5/2014 | Simpson et al. | |
| 2002/0121316 A1 | 9/2002 | Abrams et al. | |
| 2002/0147491 A1 * | 10/2002 | Khan | A61F 2/95 623/1.11 |
| 2003/0120181 A1 | 6/2003 | Toma et al. | |
| 2004/0167440 A1 * | 8/2004 | Sharrow | A61M 25/0108 600/585 |
| 2005/0137501 A1 | 6/2005 | Euteneuer et al. | |
| 2006/0047223 A1 | 3/2006 | Grandfield et al. | |
| 2007/0239259 A1 | 10/2007 | Boylan | |
| 2008/0077049 A1 | 3/2008 | Hirshman | |
| 2009/0105654 A1 | 4/2009 | Kurth et al. | |
| 2009/0227900 A1 * | 9/2009 | Kim | A61M 25/09 600/585 |
| 2009/0227902 A1 | 9/2009 | Simpson et al. | |
| 2011/0118735 A1 | 5/2011 | Abou-Marie et al. | |
| 2012/0041342 A1 | 2/2012 | Purtzer | |
| 2012/0203207 A1 | 8/2012 | Northrop et al. | |
| 2013/0046286 A1 | 2/2013 | Simpson | |
| 2013/0204163 A1 | 8/2013 | Simpson | |
| 2015/0051696 A1 | 2/2015 | Hou et al. | |
| 2015/0094616 A1 | 4/2015 | Simpson et al. | |
| 2015/0094690 A1 | 4/2015 | Simpson et al. | |

FOREIGN PATENT DOCUMENTS

| | | |
|---|---|---|
| EP | 0519604 | 5/1992 |
| EP | 0806220 | 11/1997 |
| EP | 1388350 | 2/2004 |
| EP | 2022529 | 2/2009 |
| JP | H 10-66727 | 3/1998 |
| JP | 2002503529 | 2/2002 |
| JP | 2007515259 | 6/2007 |
| WO | WO 91/15152 | 10/1991 |
| WO | WO 94/20165 | 9/1994 |
| WO | WO 99/42158 | 8/1999 |
| WO | WO 2006/002199 | 1/2006 |
| WO | WO 2010/107798 | 9/2010 |
| WO | WO 2012/058302 | 5/2012 |
| WO | WO 2013/114985 | 8/2013 |
| WO | WO 2015/048750 | 4/2015 |

OTHER PUBLICATIONS

U.S. Appl. No. 14/042,321, filed Dec. 15, 2015, OA.
U.S. Appl. No. 14/042,321, filed Jun. 10, 2016, Office Action.
U.S. Appl. No. 14/042,321, filed Jan. 10, 2017, Office Action.
U.S. Appl. No. 14/042,321, filed Jun. 1, 2017, Office Action.
U.S. Appl. No. 14/042,321, filed Mar. 7, 2018, Office Action.
U.S. Appl. No. 14/499,856, filed Sep. 16, 2016, Office Action.
U.S. Appl. No. 14/499,856, filed Apr. 12, 2017, Office Action.
U.S. Appl. No. 14/042,321, filed Sep. 4, 2018, Office Action.

* cited by examiner

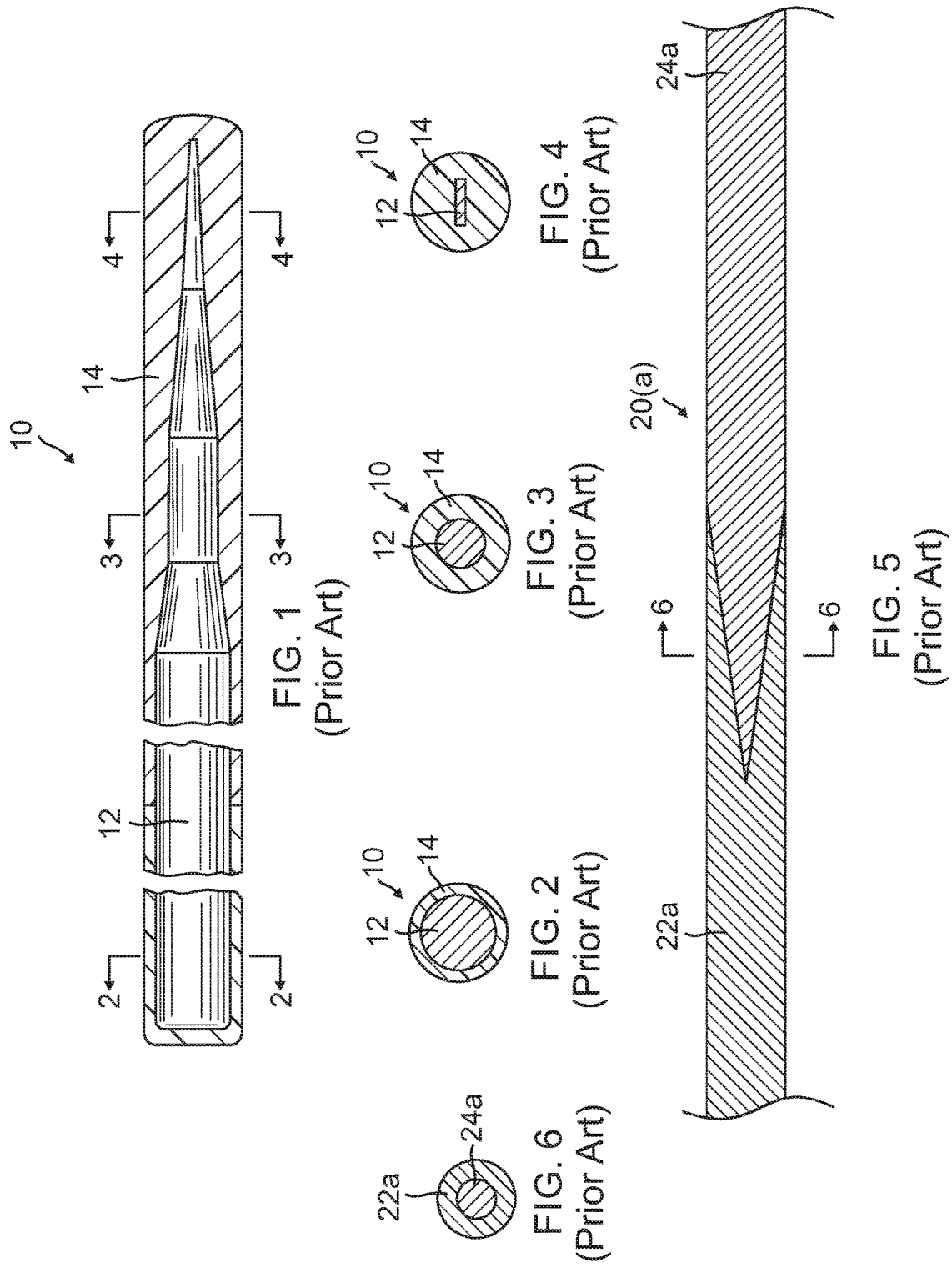

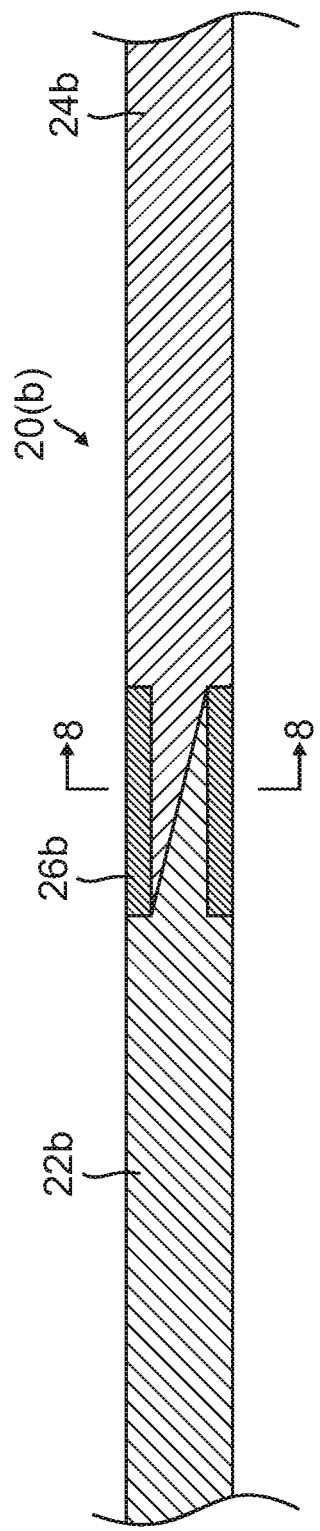
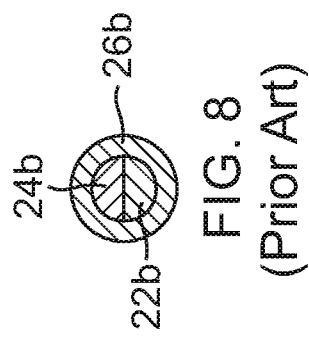
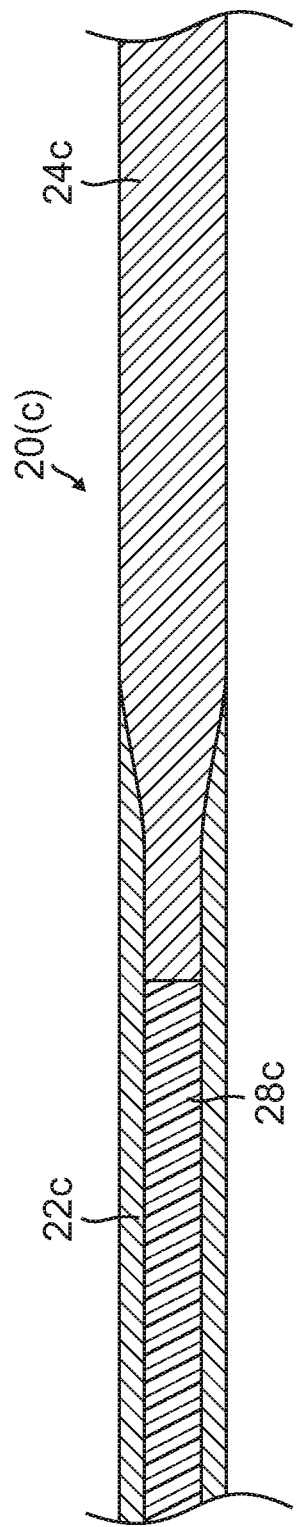
FIG. 7 (Prior Art)
FIG. 8 (Prior Art)
FIG. 9 (Prior Art)

GUIDEWIRE WITH VARYING PROPERTIES

The present application is a continuation-in-part of U.S. application Ser. No. 14/042,321, filed Sep. 30, 2013, the contents of which are incorporated herein in their entirety.

BACKGROUND

The application relates to guidewires configured for intraluminal application in medical procedures, and methods of their manufacture. More specifically, the application relates to guidewires that possess varying properties of flexibility and torsional stiffness along their length, and methods for making them.

Guidewires have long been known and used in the art of minimally invasive medical practice. Guidewires are typically used in conjunction with catheters in a procedure under which a placement catheter may first be threaded into the vasculature of a patient to a desired location using known techniques. A lumen within the placement catheter permits the physician to insert a guidewire through the catheter to the same location. Thereafter, when the physician may need to sequentially place a second, or third, or even a fourth catheter to the same location, it is a simple matter to withdraw the catheter while leaving the guidewire in place. After this action, second, third, and fourth etc. catheters may be sequentially introduced and withdrawn over the guidewire that was left in place. In other techniques, a guidewire may be introduced into the vasculature of a patient without the assistance of a placement catheter, and once in position, catheters may be sequentially inserted over the guidewire as desired.

It is typical that best medical practice for anatomical insertion requires a guidewire that has behavioral characteristics that vary along its length. For example, under some conditions, the distal end of the guidewire may be required to be more flexible than the proximal end so that the distal end may more easily be threaded around the more tortuous distal branches of the luminal anatomy. Further, the proximal end of the guidewire may be required to have greater torsional stiffness than the distal end because, upon rotation of the guidewire, the proximal end must carry all the torsional forces that are transmitted down the length of the guidewire, including what is required to overcome cumulative frictional losses.

Finally, the distal end of a guidewire should be selectively formable, so that the treating physician may apply a curve to the tip of the guidewire in order to facilitate navigation along the tortuous passageways of the vascular anatomy. By selectively formable, it is meant that the wire from which guidewire core is made may be bent to a particular shape and that the shape will be maintained by the wire. This allows the physician to impart a particular shape to the guidewire, by bending or kinking it for example, to facilitate steering its placement into a patient's vasculature. To provide this selective formability, in typical embodiments, the entire core wire may be made of stainless steel. However, other materials may be used to provide this feature. The use of a formable material, such as stainless steel, provides advantages in the guide wire over materials that cannot be formed, such as superelastic materials like Nitinol. Superelastic materials like Nitinol are so resilient that they tend to spring back to their original shape even if bent, thus are not formable. Although superelastic material may be provided with a "preformed" memory shape, such a preformed shape is typically determined in the manufacture of the guide wire and cannot readily be altered or modified by the physician by simply bending the guide wire prior to use. Although use of superelastic materials such as Nitinol in guide wire applications may provide some advantages in certain uses, a formable core, such as of stainless steel, which can be formed by the physician to a shape suitable for a particular patient or preferred by that physician, provides an advantage that cannot be obtained with a superelastic core guide wire.

Thus, certain solutions have been developed in the prior art to address these requirements. In one typical solution, a guidewire may be fabricated by applying the same metallurgical process along the entire length of an initial ingot of uniform metallurgical properties and uniform diameter that will be converted into the guidewire. The initial ingot may be taken up and cold worked along its entire length, or annealed, or swaged, or whatever process is required to impart the desired characteristics to the metal of the final guidewire product. Once these metallurgical processes have been performed on the wire as a whole, the wire obtained from the worked ingot may be geometrically shaped in order to impart desired different flexibilities, torsional stiffnesses and the like that are desired in the final guidewire product. For example, the wire obtained from a worked ingot may be shaped by known process such as chemical washes, polishes, grinding, or compressing, to have a distal end with a diameter that is smaller than the diameter of the proximal end. By this means, the distal end will be given greater flexibility but less torsional resistance than the proximal end. A shaped guidewire 10 of the kind described is depicted in FIG. 1 where it may be seen that a core metal element 12 having a configuration with varying diameter sizes along its length is coated in a polymer 14, or other suitable material. The coating may be configured to impart a more uniform outside diameter to the overall guidewire 10. Alternatively, one or more wire coils may be used instead of or in conjunction with a polymer coating for similar purpose.

In another typical solution, different pieces of wire may be formed by different processes to have different properties. These pieces of wire may then be joined or connected together into a single guidewire core using known jointing processes, to provide a resulting guidewire with varying properties along its length. For example, as may be envisaged with reference to FIG. 5 through FIG. 9, different embodiments 20a, 20b, and 20c show how a superelastic portion of wire 22a, 22b, and 22c made from Nitinol or similar metal, may be joined to a portion of wire 24a, 24b, and 24c that has linear elastic properties using joining methods such as welding, soldering, brazing, or covering with a jacket 26b, or inserting a filler 28c. These types of joints between portions of a wire having different metallurgical properties are referred to herein as "mechanical" joints. These mechanical joints are to be distinguished from interfaces (that will be described in the invention below) between different portions of a single unitary wire which have different metallurgical properties arising from having different metallurgical processes applied to those portions while still part of the single unitary wire.

Thus, in a core wire having this combination of a distinct and mechanically joined formable distal portion and a superelastic proximal portion, desired shapes may be imparted by a physician to the distal end of the guide wire to facilitate making turns, etc., in tortuous vessel passages, while in the same guide wire the more proximal portion would possess superelastic properties to allow it to follow the distal portion through the tortuous passages without permanently deforming.

However, problems may arise in the prior art as described. Welds and solder or braze joints are generally undesirable on a guidewire because they introduce a potential point of kinking or fracture. Furthermore, discrete steps in the gradient of a guidewire diameter that are introduced by grinding or other known means may also introduce potential points at which stress is raised to produce cracking or fracture.

Thus there is a need in the art for a system and method for a guidewire that solves the problems in the prior art. The present invention addresses these and other needs.

SUMMARY OF THE INVENTION

In some preferred embodiments, the invention is a method for making a core metal element for a medical guidewire. In a first embodiment, the method comprises providing a wire of nickel titanium alloy with superelastic properties having a proximal end and a distal end, wherein a first length separates the proximal end from the distal end; applying cold work to the wire through a rotary swaging machine in a sequence that comprises swaging the wire over a second length of the wire that includes the distal end by using a die set having a first diameter; and then, swaging the wire over a third length of the wire that includes the distal end by using a die set having a second diameter, the third length being less than the second length, and the second diameter being less than the first diameter. In some embodiments the second length may be between 20 mm and 16 mm, and the third length may be between 14 mm and 10 mm. Further, in embodiments, the first diameter may be between 0.436 mm and 0.356 mm, and the second diameter may be between 0.425 mm and 0.347 mm. In some embodiments, the wire may be swaged over a fourth length of the wire that includes the distal end by using a die set having a third diameter, the fourth length being less than the third length and the third diameter being less than the second diameter. After these steps are complete a reducing process may be applied to the wire, whereby the wire may be reduced to having a constant diameter over the first length. A method of applying a reducing process to the guidewire may comprise applying centerless grinding. In some aspects of the invention, the second length may be less than the first length, and this may apply where only the tip of the wire is formed in the manner described.

In another aspect, the invention may comprise a method of making a core metal element for a medical guidewire comprising providing a wire of nickel titanium alloy with superelastic properties having a proximal end and a distal end, wherein a first length separates the proximal end from the distal end, and applying cold work to the wire through a rotary swaging machine in a sequence that comprises swaging the wire over a second length of the wire between a first distal point and a first proximal point by using a die set having a first diameter; thereafter, swaging the wire over a third length of wire between a second distal point and a second proximal point by using a die set having a second diameter, the second diameter being larger than the first diameter, and wherein the second distal point coincides with the first proximal point. In some aspects of this embodiment, the second length may be between 8 mm and 4 mm, and the third length may be between 8 mm and 4 mm. Further, the first diameter may be between 0.414 mm and 0.338 mm, and the second diameter may be between 0.425 mm and 0.347 mm. In some embodiments, the first distal point coincides with the distal end. Under the foregoing steps, in some embodiments, the invention comprises swaging the wire over a fourth length of the wire between a third distal point and a third proximal point by using a die set having a third diameter, the third diameter being larger than the second diameter, and wherein the third distal point coincides with the second proximal point.

In a further aspect, the invention is a method of making a core metal element for a medical guidewire comprising providing a wire of nickel titanium alloy with superelastic properties having a proximal end and a distal end, wherein a first length separates the proximal end from the distal end, applying cold work to the wire through a rotary swaging machine in a sequence that comprises: swaging the wire over a second length of the wire that includes the distal end by using a die set having a certain diameter; and swaging the wire over a third length of the wire that includes the distal end by using the die set, the third length being less than the second length. In some embodiments, the second length may be between 20 mm and 16 mm, and the third length may be between 14 mm and 10 mm. Additionally, the certain diameter may be between 0.414 mm and 0.338 mm. Under the foregoing, the invention may further include swaging the wire over a fourth length of the wire that includes the distal end by using the die set, the fourth length being less than the third length.

In yet a further aspect, the invention may be a method of making a core metal element for a medical guidewire comprising: providing a wire of nickel titanium alloy with superelastic properties having a proximal end and a distal end, wherein a first length separates the proximal end from the distal end; applying cold work to the wire through a rotary swaging machine in a sequence that comprises: swaging the wire over a second length between a first proximal point and a first distal point, by using a die set having a certain diameter and feeding the wire through the die set at a first feed rate; and swaging the wire over a third length between a second proximal point and a second distal point by using the die set and feeding the wire through the die set at a second feed rate, the second feed rate being faster than the first feed rate, wherein the second distal point coincides with the first proximal point. The first distal point may coincide with the distal end of the wire. In some embodiments, the second length may be between 8 mm and 4 mm, and the third length may be between 8 mm and 4 mm. In further embodiments, the certain diameter may be between 0.414 mm and 0.338 mm. In yet further embodiments, the first feed rate may be between 1.25 mm/rev. and 0.750 mm/rev., and the second feed rate may be between 0.625 mm/rev. and 0.375 mm/rev. Under the above, some embodiments, may further include swaging the wire between a third proximal point and a third distal point by using the die set and feeding the wire through the die set at a third feed rate, the third feed rate being faster than the second feed rate, wherein the third distal point coincides with the second proximal point.

In yet a further embodiment, the invention is a guidewire for medical use. The guidewire comprises a metal core having a proximal end and a distal end, wherein the metal core includes a proximal portion having superelastic properties; a distal portion having linear elastic properties, wherein the distal portion includes the distal end; and wherein, the metal core does not include a mechanical joint at any location between the proximal end and the distal end. A mechanical joint is described above, and it is a joint between initially separate portions of metal that are subsequently joined together by welding, soldering, brazing, covering with a jacket, or inserting a filler. The absence of a mechanical joint is important for the invention because a mechanical joint has the tendency to create a location for stress raising which may cause crack propagation, and brittle fracture. In some embodiments, the metal core has a constant diameter between the proximal end and the distal end. In some embodiments, the distal portion is between 4 mm and 8 mm in length. In yet further embodiments, the metal core further includes an intermediate portion that is positioned between the proximal portion and the distal portion, the intermediate portion having properties that are a combination of superelastic properties and linear elastic properties. In this regard, the proximal portion will have had no cold work applied to it, but the distal portion will have been cold worked to impart linear elastic properties. The intermediate portion will have had some cold work applied to it, but not as much cold working energy will have been applied as was applied to the distal portion. This aspect provides the core with a graduated degree of cold working towards the distal end, and allows a tip to be formed by a surgeon that has a varying radius, with the smallest radius of curvature at the distal terminal end. In some embodiments, the intermediate portion is between 4 mm and 8 mm in length. and may be formed of is formed from a nickel titanium alloy. In preferred embodiments, the distal portion includes a metal to which the linear elastic properties have been imparted by a process of cold working.

These, and further advantages of the invention will become apparent when read in conjunction with the figures and the detailed description of the preferred embodiments.

BRIEF DESCRIPTION OF THE DRAWINGS

FIG. 1 shows a partial sectional view of a prior art guidewire with a sequence of diameter reductions, shown in shortened schematic form.

FIG. 2 is a sectional view through the guidewire of FIG. 1, taken substantially along the line 2-2 in FIG. 1.

FIG. 3 is a sectional view through the guidewire of FIG. 1, taken substantially along the line 3-3 in FIG. 1.

FIG. 4 is a sectional view through the guidewire of FIG. 1, taken substantially along the line 4-4 in FIG. 1.

FIG. 5 shows a sectional view of a prior art guidewire with proximal and distal portions joined together.

FIG. 6 is a sectional view through the guidewire of FIG. 5, taken substantially along the line 6-6 in FIG. 5.

FIG. 7 shows a sectional view of a prior art guidewire with proximal and distal portions joined together.

FIG. 8 is a sectional view through the guidewire of FIG. 7, taken substantially along the line 8-8 in FIG. 7.

FIG. 9 shows a sectional view of a prior art guidewire with proximal and distal portions joined together.

DETAILED DESCRIPTION OF THE EMBODIMENTS

Figure 10:
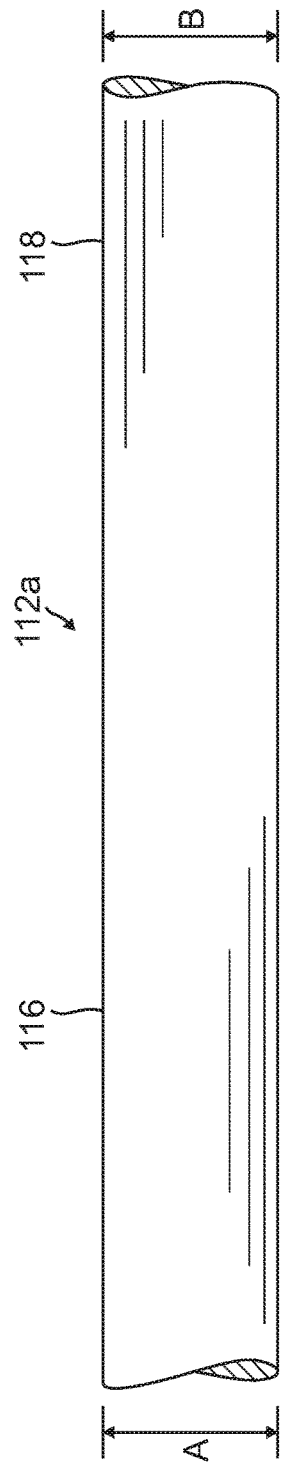
FIG. 10 is a schematic side view of a wire in a first condition in the process of preparation for use according to an embodiment of the present invention.

In conjunction with the figures, there is described herein a medical guidewire and a method for manufacturing a medical guidewire having features of an embodiment of the present invention. In some embodiments, the invention includes a method for forming a core for a guide wire of an embodiment according to the present invention.

In its final form, the guidewire may comprise an elongated solid core wire 112 and an outer jacket 114 made from a polymer with lubricious, or with hydrophilic or even with hydrophobic qualities, depending on the needs of the situation. The elongated solid core wire 112 includes a proximal section 116 of a constant diameter, and a distal section 118.

The core wire may preferably be made of a NiTi alloy. In some embodiments, the NiTi alloy useful for the present invention may be initiated by preparing an ingot which may be melted and cast using a vacuum induction or vacuum arc melting process. The ingot is then forged, rolled and drawn into a wire. In some embodiments, exemplified in FIG. 10, the resulting core wire 112a may have a diameter of about 0.030 inches in diameter, and may have a nominal composition of about 55.0 weight percent Ni and an austenite transformation start (As) temperature of about 0 degree C. in the fully annealed state. In this form, the wire may exhibit superelastic properties at a body temperature of about 37 degree C., which are desirable in at least portions of a guidewire so that those portions do not permanently deform as they are extended through a tortuous anatomy.

Once the initial basic wire 112a has been thus prepared, a length of wire that is desired to possess linear elastic properties is identified and selected. With reference to FIGS. 11 to 14, this selected length is identified by the reference numeral 118 and is referred to herein as the distal portion of the wire. A portion of the wire that is not desired to possess linear elastic properties, but to retain its superelastic properties, is identified by the numeral 116 and is referred to herein as the proximal portion. In some embodiments, the proximal portion 116 and the distal portion 118 are selected to be adjacent to each other, but this is not a limiting requirement of the invention. In fact, portions of the wire between the proximal portion 116 and the distal portion 118 may be selected for yet further and different treatment than that set forth herein below. In this initial condition, the wire is configured so that the proximal portion has a diameter "A," and the distal portion may have a second diameter "B" as shown in FIG. 10. In some embodiments, the first diameter A is the same as the second diameter B, while in other embodiments these diameters may purposely differ and may have a gradual taper between them.

Figure 11:
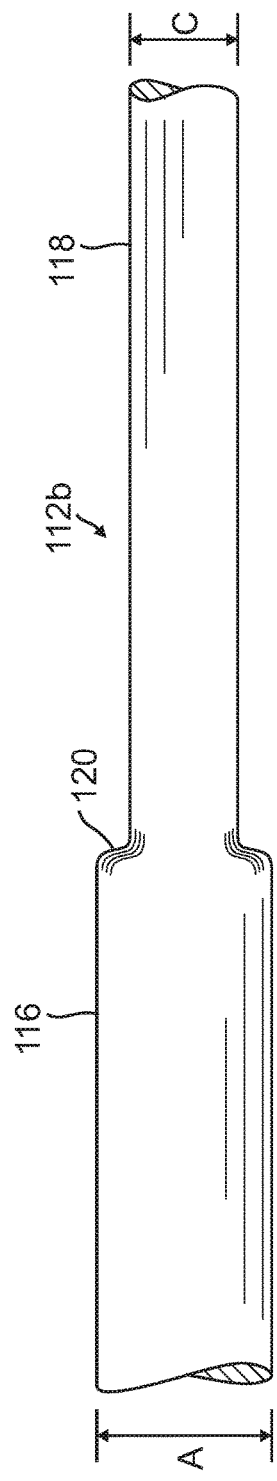
FIG. 11 is a schematic side view of a wire in a second condition in the process of preparation for use according to an embodiment of the present invention.

In either case, the following manufacturing steps may be performed. Cold work may be applied to the distal portion 118 of the wire, without applying cold work to the proximal portion 116 of the wire. By applying cold work to the distal portion 118, the diameter of the distal portion is given a third diameter "C" that is less than the second diameter "B", as seen in FIG. 11. In some embodiments, the cold work may be applied by drawing the distal portion through a die and then removing it by reverse drawing. This overall process may further include removing the wire from the die without drawing the distal portion 118 back through the die, such as by using a multiple-piece die which can be opened to enable wire removal, In other embodiments, applying cold work to the distal portion may include methods selected from swaging, tensioning, rolling, stamping, and coining. In some embodiments, swaging may utilize a set of two or more revolving dies which radially deform the workpiece repeatedly as it passes between the dies. Like wiredrawing, swaging can produce an essentially round cross-section of reduced diameter. However the resulting work hardening is typically non-uniform across its final cross-section due to the so-called "redundant work" caused by repeated re-ovalization as the revolving dies repeatedly strike the non-revolving workpiece (which may be in 60° increments, in some embodiments). The final distribution of cold work may be influenced by both feed rate and die strike rate, and likely also by the contact length of the die set. Hence, judicious selection of processing conditions is required to attain the desired distribution of cold work within the distal section of the Nitinol core wire before grinding to final size.

Regardless of initial straightness of a wire, it is typical for as-drawn wire to become curved as a result of passing through a wiredrawing die. This can be remedied by simultaneously applying heat and tension to induce stress relaxation within the as-drawn portion. This straightening method can be applied to the present invention, provided the time and temperature are not sufficient to restore original superelastic properties, which typically takes several minutes at about 500° C. A suitable combination of tension and heat may be determined through experimentation, with the goal of attaining suitable straightness for a drawn portion, which persists after producing the final guide wire core profile. Alternatively, torsional deformation may be imparted to the drawn portion, thereby generating a symmetric gradient in shear strain which eliminates the curvature in said portion by overriding the generally asymmetric residual stress state produced by wire drawing.

Once the wire is given satisfactory metallurgical properties by differential treatments such as those described, it will be appreciated that the wire may have a stepped shoulder 120 as exemplified by wire 112b seen in FIG. 11, where the distal portion 118 may have linear elastic properties, and the proximal portion 116 may retain the original superelastic properties inherent in the unworked nickel titanium alloy. It will be appreciated that the step 120 seen in FIG. 11 may have a steep stepped gradient, or a more gently sloping gradient, depending on the precise process by which cold work is applied to the distal portion 118.

Figure 12:
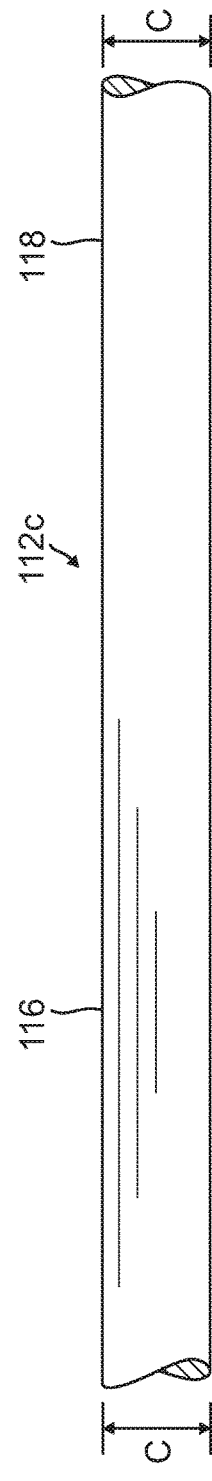
FIG. 12 is a schematic side view of a wire in a third condition in the process of preparation for use according to an embodiment of the present invention.
Figure 13:
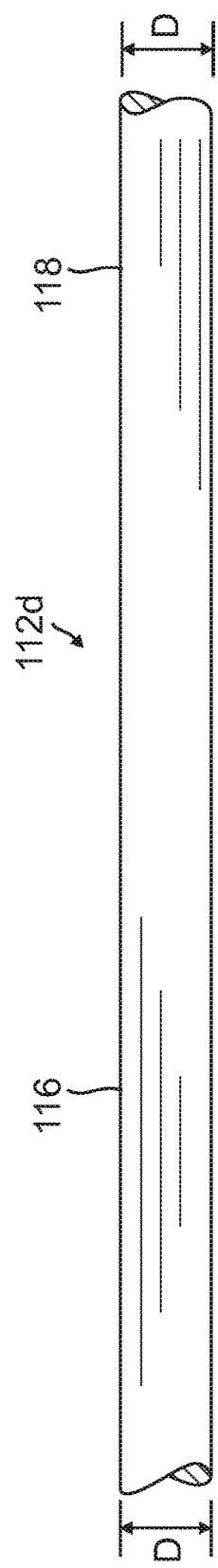
FIG. 13 is a schematic side view of a wire in a fourth condition in the process of preparation for use according to an embodiment of the present invention.

In a subsequent stage, the wire may then be subjected to a reducing process, in which the step 120, (i.e., the differential diameter between the proximal portion 116 and the distal portion 118) is removed. In this stage, the step 120 may be removed to impart the proximal portion 116 of the wire 112c to have a diameter "C" that is the same as the existing third diameter "C" of the distal portion 118, as seen in FIG. 12. Alternatively, the wire 112d may be further reduced so that both proximal and distal portions are reduced so that each has have a fourth diameter "D" that is smaller than diameter "C", as seen in FIG. 13.

In some embodiments, the process of reducing the wire may be the known process of centerless grinding, which is a machining process that uses abrasive cutting to remove material from a workpiece. In some forms of centerless grinding, the workpiece is held between a workholding platform and two wheels rotating in the same direction at different speeds. One wheel, known as the regulating wheel, is on a fixed axis and rotates such that the force applied to the workpiece is directed downward, against the workholding platform. This wheel usually imparts rotation to the workpiece by having a higher linear speed than the other wheel. The other wheel, known as the grinding wheel, is movable. This wheel is positioned to apply lateral pressure to the workpiece, and usually has either a very rough or a rubber-bonded abrasive to grind away material from the workpiece. The speed of the two wheels relative to each other provides the rotating action and determines the rate at which material is removed from the workpiece by the grinding wheel. During operation the workpiece turns with the regulating wheel, with the same linear velocity at the point of contact and (ideally) no slipping. The grinding wheel turns faster, slipping past the surface of the workpiece at the point of contact and removing chips of material as it passes. In other embodiments of the invention, the reducing process may include chemical washes, or polishes.

Once these reducing steps as described above are performed, the wire 112c or 112d will have a uniform diameter "C" or "D" respectively throughout the proximal portion and distal portion. It will be appreciated however that, despite its uniform geometrical shape the wire will have differential metallurgical properties in the proximal and distal portions, and hence differential flexural and torsional stiffnesses and also deformation related properties.

Figure 14:
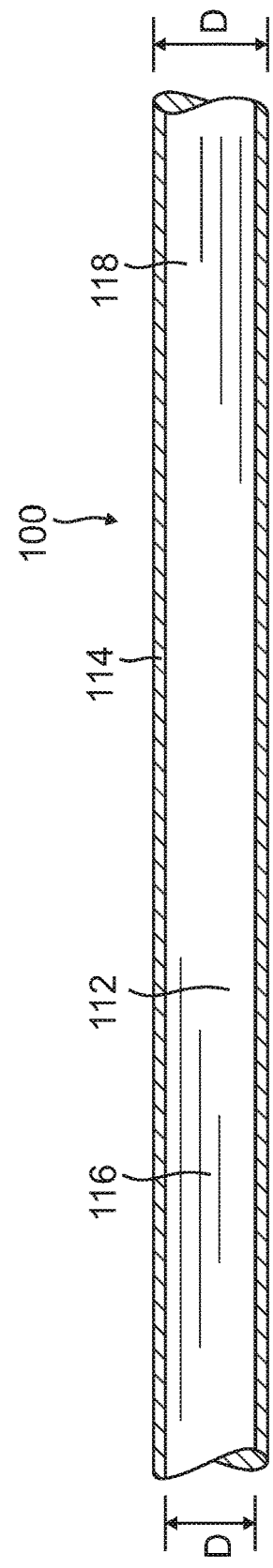
FIG. 14 is a schematic side view of a wire in a fifth condition in the process of preparation for use according to an embodiment of the present invention.

Thus, once a uniform wire of desired diameter is produced according to the methodology set forth, the wire may be coated with a suitable polymer coating 114 as seen in FIG. 14. The wire thus produced does not have unnecessary joints between portions having different metallurgical properties, and neither does it have unnecessary diametric steps between different portions. This aspect eliminates focus points or stress raising points for kinking for fracture, and results in a strong and reliable core wire that has beneficial differential properties along its length that may affect torsional stiffness while allowing differential flexibility as desired for vascular insertion. By way of example, a guide wire core wire thus produced may provide non-superelastic metallurgical properties to its extreme distal end directly after centerless grinding, without need for subsequent deformation such as flattening to impart said properties, thus enabling a fully circular cross-section with its associated rotational bending uniformity which prevents the alternating buildup then release of stored elastic energy, known as "whipping", when the guide wire is rotationally manipulated in tortuous anatomy.

As used herein, the terms proximal and distal do not necessarily reflect a proximal-most portion or a distal-most portion of a guidewire element. Rather, these terms are used to indicate the position of one portion in relation to another.

Additional portions may be added to either end of a proximal or a distal portion and that are not subjected to the processes set forth herein.

In further embodiments of the invention, a novel and advantageous method may be used of applying cold work to a core wire through a rotary swaging process. A particularly useful application for this aspect of the invention is intended to enhance the utility of guide wires by making the most distal section of a guide wire tip more "shapeable" than its remainder. Doing so makes it easier for the user to produce an extremely short or "micro"—J or—L shape at the very tip, and also enables the user to produce an overall tip shape with varying curvature. In the latter situation, the imparted curvature would generally be more extreme at the very tip and less extreme but more durable elsewhere along the guide wire tip.

Figure 15:
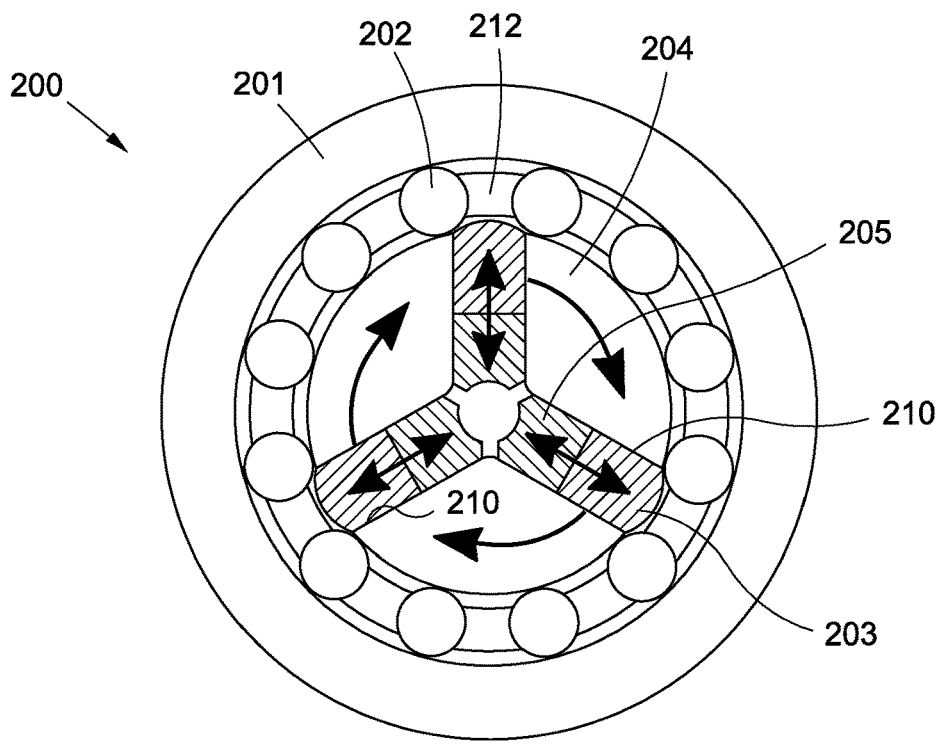
FIG. 15 is a schematic image, front elevation, of a known rotary swaging machine, shown in a first condition with dies open.
Figure 16:
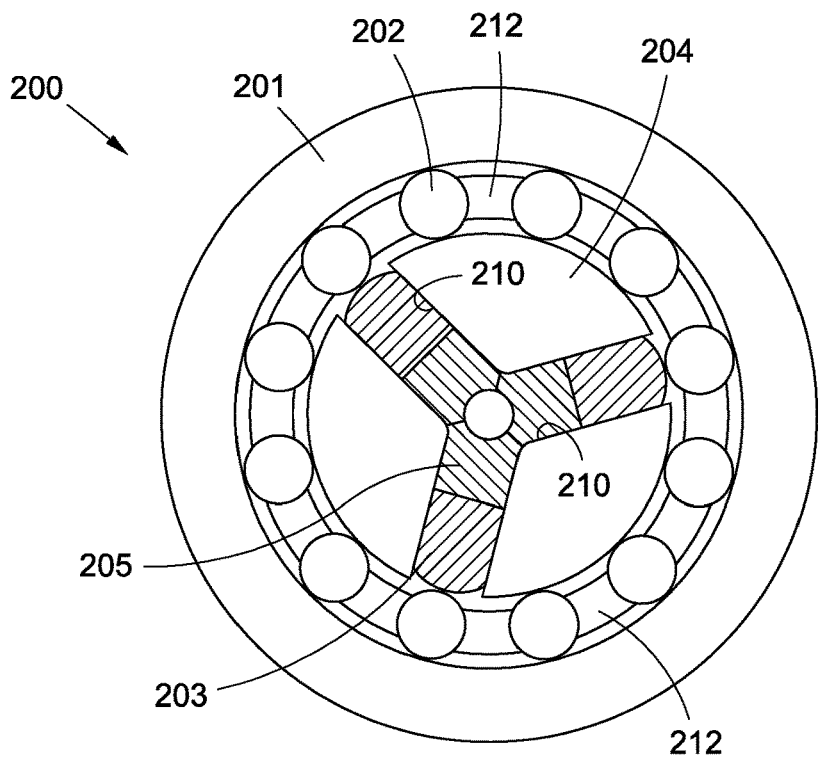
FIG. 16 is a schematic image, front elevation, of the swaging machine of FIG. 15, shown in a second condition with dies closed.

Rotary swaging machines are known in the art, and are generally described here with reference to FIGS. 15-16. These figures show the principle of operation of a classical rotary swager 200. While such systems are known, the novelty in the present invention resides in the method of applying cold work to the guidewire during fabrication through a rotary swager, as described in more detail below.

A rotary swager 200 comprises a head cylinder 201 which is fixed to a mounting (not shown). A cylindrical spindle 204 is provided and is configured to be rotated (by motor, not shown) on an axis which is co-axial with that of the head cylinder 201. The spindle is provided with linear slots 210 aligned radially, in order to hold a plurality of backers 203 and dies 205. Both backers and dies are configured to slide within the slots 210.

A special bearing system is provided, and is positioned between the head 201 and the spindle 204. The bearing system comprises a support 212 which is cylindrical in profile, but contains a plurality of openings sized to receive rollers 202 which are cylindrical. The rollers have a diameter that is slightly larger than the radial thickness of the cylindrical support 212. As may be envisaged with reference to FIGS. 15-16, as the spindle 204 rotates within the head cylinder 201, the backers 203 are passed over the rollers 202. It will be appreciated that, due to the larger diameter of the rollers, the rollers will impart a radially inward blow to the backers 203 as the backers rotate past the rollers. This blow will, in turn, pass a radially inward blow to the dies 205.

By this mechanism a series of radially inward simultaneous blows are provided to the dies 205, so that the dies advance to a closed condition, shown in FIG. 16, over the workpiece (not shown in FIGS. 15-16) to impart cold work to the workpiece and to form the material. When the backers 203 are located between two roller positions, centrifugal forces will move the backers (and hence also the dies) radially outward so that the dies assume an open condition as shown in FIG. 15. The operation continues a number of times and the result is a reduced round cross section of the workpiece which may be a tube, bar or wire. The dies 205 define an inwardly facing circular surface having a set diameter which is selected to suit a workpiece to be fed through the swager and coaxially with the swager. As seen in FIG. 16, the circular surface may be closed in a full continuous circle when the dies are forced to a closed position, but when the dies are open as seen in FIG. 15, the dies form a discontinuous circular surface. However, when a workpiece is positioned inside the dies, the dies will naturally not form a full continuous circular surface when they are closed, because the workpiece will be selected to be larger than the diameter of the inwardly facing surface.

Figure 21:
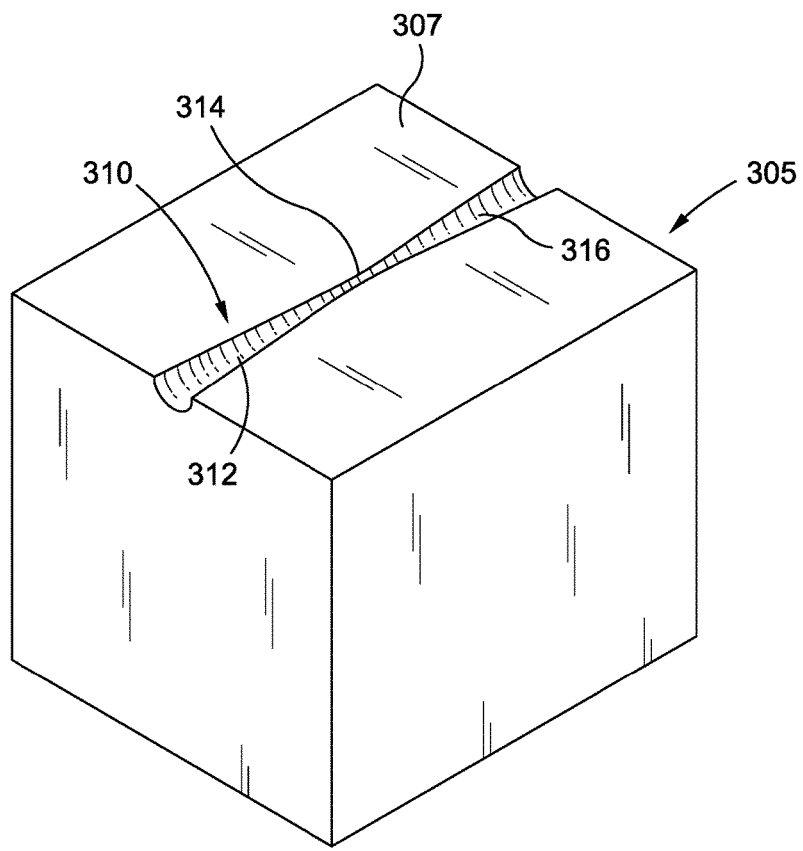
FIG. 21 is a perspective view of a single die, configured to be used in conjunction with an opposing die, suitable for carrying out the method of the invention.
Figure 22:
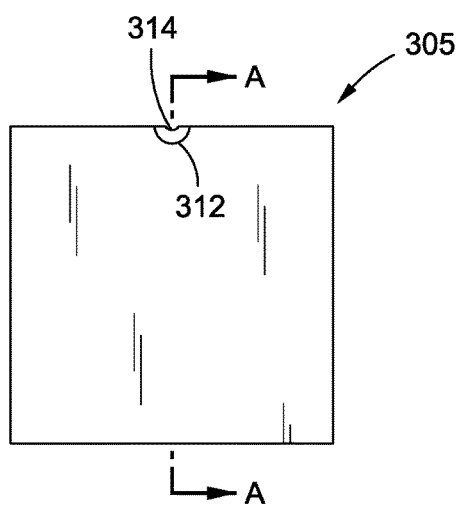
FIG. 22 is an end view of the die shown in FIG. 21.
Figure 23:
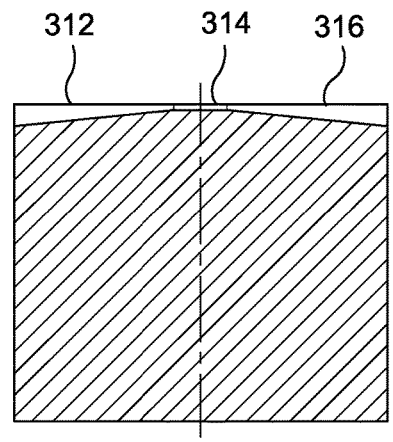
FIG. 23 is a sectional view of the die shown in FIG. 22, taken substantially along the line A-A in FIG. 22.

In another rotary swaging device, exemplified in FIGS. 21-23, a rotary swaging machine has only two dies 305 which are configured to slide within two slots, and which are positioned directly opposite each other (that is, at 180 degrees to each other) around a rotary swager of the general kind seen above in FIGS. 15-16 but modified accordingly. A suitable swaging machine for this purpose is the rotary swaging machine by the Torrington Company, available as the Series 100, 111, or 211 each of which is suitable for swaging small rods and tubes. Available from Torrington in Waterbury, Conn. 06704.

Each die 305 of the two part, die set has a contact surface 307 which, under certain conditions depending on the size of the workpiece, may come into contact with a mating surface of an opposing die during a die strike. Extending axially along the contact surface 307 is a shaping channel 310. The shaping channel is a compound shape comprising three contiguous portions. A proximal portion 312 has a shape that, when positioned adjacent the opposing die, produces a generally frustoconical shape with an apex angle configured to feed a workpiece axially along the die set without damage to the workpiece. Adjacent the proximal portion is a strike portion 314 which, when adjacent the mating die, produces a generally cylindrical shape. The cylinder is not exactly circular in cross section, but may have a slightly ellipsoid cross section so that metal that is struck by the strike portion 314 at the location of the minor axis of the ellipse has room to deform into the area provided by the major axis. Selection of the precise shape of the elliptical cross section may be established by initial test runs to identify a shape that produces desirable behavioral characteristics in the workpiece. As its name implies, the strike portion 314 is the portion which carries out the cold work on the workpiece by striking the workpiece from opposite sides, and in preferred embodiments the length of the strike portion may be configured to be in a ratio to the diameter of the strike portion of between 3:1 and 10:1. Finally, adjacent the strike portion 314 is a distal portion 316 which produces a generally frusto-conical shape in the same way as the proximal portion 312, and this shape allows the workpiece to depart from the vicinity of the strike portion without injury to the workpiece.

Turning now to novel methods of using a rotary swager in the process of forming a guidewire to have stiffness properties that vary along its length, the following steps may be advantageously applied to a guidewire core wire as the workpiece. This process will impart a varying level of cold work along the overall swaged lengths before the core wire is ground down to a final profile using methods described above.

In particular, this method is advantageous in applying a varying degree of cold work to the distal tip of a guidewire. For it is to the distal tip that a surgeon will wish to give a bent shape before he inserts it into the vasculature of a patient. More particularly, the surgeon will typically want the very distal tip, approximately the last 5 mm, to have a greater curvature than the next 5 mm proximal to that portion, and again this portion to have a greater curvature than the next 5 mm proximal to that portion. (Noting here that curvature is defined as the reciprocal of the radius of curvature, so that the smaller the radius of curvature, the greater the curvature itself.) Thus, where a surgeon is provided with a guidewire in which the distal tip has been fashioned to have such varying amounts of cold work, he may use a single hand movement to impart a varying degree of curvature to the distal tip. With one twist of the thumb and the forefinger, the surgeon may rotate the distal tip around this thumb, and then release it. This action will impart a constant torque to the last inch or so of the guidewire, but due to the varying elastic modulus in the tip imparted by these novel methods, the resulting inelastic curvature will increase towards the end of the tip. This result is advantageous in that the surgeon, who is typically preoccupied with a number of tasks at the time he gives the distal tip a shape that he wants, is able to provide this shape with a single movement of the hand.

First Embodiment

In some embodiments, a technique is followed whereby different die sizes are used to impart different swaged diameters, and different amounts of cold work, to the core wire. In a first embodiment following this technique, a core guidewire workpiece is rotary swaged multiple times in order of decreasing die size. Specifically, a distal portion of the wire (which may in some embodiments substantially comprise the entire length of the wire), may first be swaged using the largest die size. Thereafter, a shorter length that includes the distal end of the distal portion may be swaged using a smaller die size. Again, an even shorter length of the distal portion may be swaged using an even smaller die size, and so on until the last swaging operation is complete. Because a smaller die size produces a greater percentage reduction of diameter for a given initial wire diameter, the most distal section will experience the most cold work and will therefore be the most shapeable. It will be appreciated that, once the swaging is complete, the wire will have a gradually tapering profile (which may include a stepped taper), with a larger diameter at the proximal end, and a smaller diameter at the distal end, but where the distal end has been given the largest amount of cold work energy. At this stage, the wire may be ground, using techniques described above, to provide a guidewire having substantially constant diameter, but having different degrees of shapeablity along its length, with the most shapeable being at the distal end where the cold work energy has been greatest.

Figure 17:
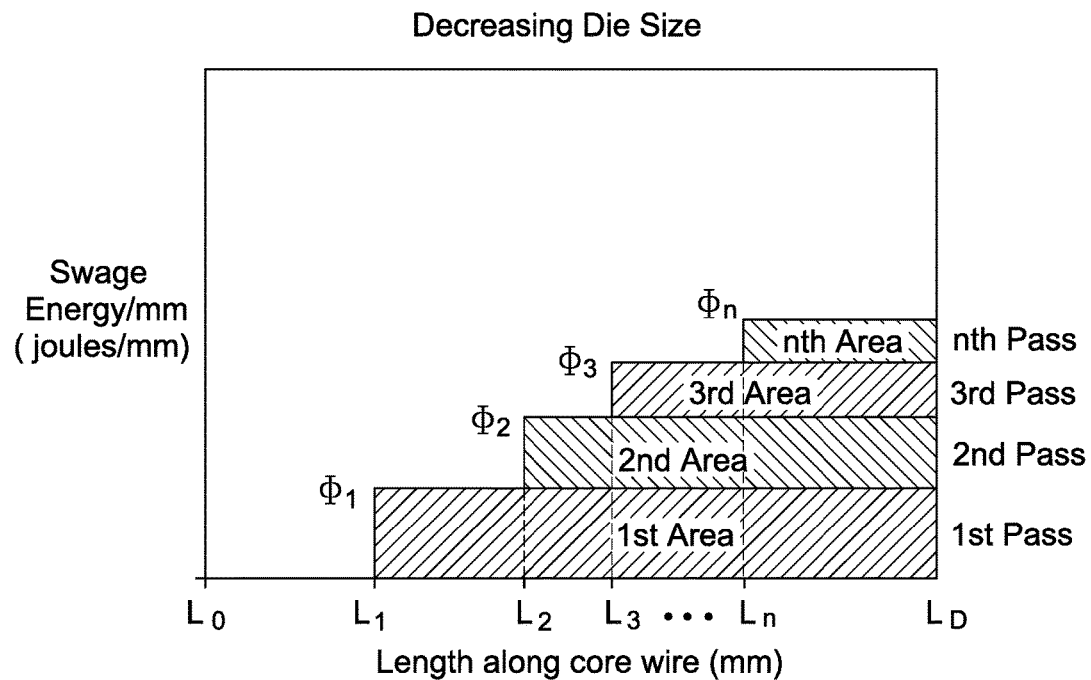
FIG. 17 is a schematic graph exemplifying how a method for fabricating a guidewire of one embodiment is applied to a core wire.

FIG. 17 is a graph clarifying, by example, how the technique of this embodiment may be applied to a core wire in order to produce a guidewire with advantageous properties. The horizontal axis of the graph reflects the length (mm) along a core wire from the proximal end L0; and the vertical axis reflects the cumulative amount of energy per unit length (joules/mm) applied to the core wire through cold working by rotary swaging. As can be understood from FIG. 17, a rotary swager having a die set with diameter $\Phi 1$ (all diameters herein are expressed as the minor axis of a generally elliptical shaped strike portion 314 of the die) is selected for first application of cold work. This diameter $\Phi 1$ will be the largest diameter selected during the process of this embodiment. Starting at a length L1 from the distal end of the core wire (the proximal end starts at the origin, L0), the core wire is fed through the rotary swager so that cold work energy via rotary swaging is applied to core wire between L1 and the distal end, LD. (Optionally, in some embodiments no cold work may be applied between L0 and L1, but in other embodiments, L1 may coincide with L0.) Of course, it will be appreciated that an equivalent result may be achieved, and is within the scope of the invention, if the core wire is fed through the rotary swager so that cold work energy via rotary swaging is applied to core wire in the other direction, starting at LD and progressing to L1. The same principle applies in any of the embodiments described herein, by which the die set may advance either distally or proximally within a defined space.

By way of clarification, in some operations for conducting the process of swaging, the operation does not measure or calculate swaging energy (Joules/mm). Rather, cold work is quantified by "Percentage Reduction of Area" through a calculation involving measured diameters before and after swaging. Additionally, some operations calculate the theoretical number of head revolutions that any initial cross-section within the wire experiences as it passes through the die contact zone in both direction. Although not absolute, this value is used to represent the relative degree of redundant work. This calculation involves 3 terms: head rotation speed, axial feed speed and die contact length. In the figures, the vertical axis shows energy in joules/mm, but any of these parameters will also reflect the same principles.

As will be apparent to one of ordinary skill in the art, the area marked as "$1^{st}$ Area" on the graph of FIG. 17 schematically represents the amount of energy applied to the core wire by the die set having diameter $\Phi 1$, summed up over the length of the wire between L1 and LD.

Once the core wire is fed through the rotary swager, the dies are removed, and are replaced with an alternative die set having an internal diameter $\Phi 2$, which is a diameter slightly smaller than $\Phi 1$. Then, starting from a distance L2 from the distal end (L2 being closer to the distal end than L1), the core wire is fed through the rotary swager so that cold work energy via rotary swaging is applied to core wire between L2 and the distal end, LD. As will be apparent to one of ordinary skill in the art, the area marked as "$2^{nd}$ Area" on the graph schematically represents the additional amount of energy applied to the core wire by the die set having diameter $\Phi 2$, summed up over the length of the wire between L2 and LD. As will be further apparent to one of ordinary skill in the art, the area falling within both "$1^{st}$ Area" and "$2^{nd}$ Area" now represents the cumulative energy applied by swaging under a die set having diameter $\Phi 1$ followed by swaging under a die set having diameter $\Phi 2$. Once the core is fed through the swager, a similar process may be followed by which the diameter of the die set is changed and reduced to $\Phi 3$, starting at point L3 on the wire . . . and then finally to $\Phi n$ at point Ln. It will be appreciated that the counter "n" is given its typical meaning so that, depending on the cold work required, "n" may be any number from 2 upwards and represents the number of swaging passes that are performed.

The cumulative energy per unit length applied at any point to the core wire is reflected by the schematic graph in FIG. 17, with the greatest amount of energy per unit length applied at the distal end of the core wire. It will be understood that, as a consequence of the cold work applied, the profile of the wire will become stepped down at each point L1 through to Ln, and will resemble the structure exemplified in FIG. 11 at each stepping point. Finally, just as with the embodiment in FIG. 11, the core wire may be ground using a grinding or reducing technique as described above. Thus, by a judicious selection of die set diameter sizes, and of starting points along the wire, a core wire with desired stiffness along its length and particularly at the distal end may be advantageously fabricated from a single strand of core wire.

Example 1

In applying the method of the embodiment described immediately above, the following parameters may be used to provide a core wire for a guidewire. These would provide a differentially cold worked tip suitable for receiving a bend for threading through the vasculature of a patient.

Core wire starting diameter=0.01750 inches (0.445 mm); Φ1=0.0156 inch (0.396 mm), L1 to LD=18 mm; Φ2=0.0152 inch (0.386 mm), L2 to LD=12 mm; Φ3=0.0148 inch (0.376 mm), L3 to LD=6 mm. Feed rate=0.217 mm/rev.; "n"=3 (where "n" correlates with the number of swaging passes, as clarified above).

Second Embodiment

In a further embodiment, the sequence of die size selection is reversed, so that swaging is performed in order of increasing die size. Although the approach in this embodiment and the previous embodiment may appear to produce equivalent results if their final swaged dimensions are equivalent prior to profile grinding, the previous embodiment would actually result in a greater overall level of cold work and therefore greater shapeability in the more distal sections due to the redundant work inherent in the rotary swaging process. However, through judicious die size selection relative to their resulting post-swaged wire diameters, the present embodiment may be used to purposely avoid repeat swaging within the most distal sections if so desired. That is, successive die sizes could be selected so as to clear the previously swaged sections of wire.

Figure 18:
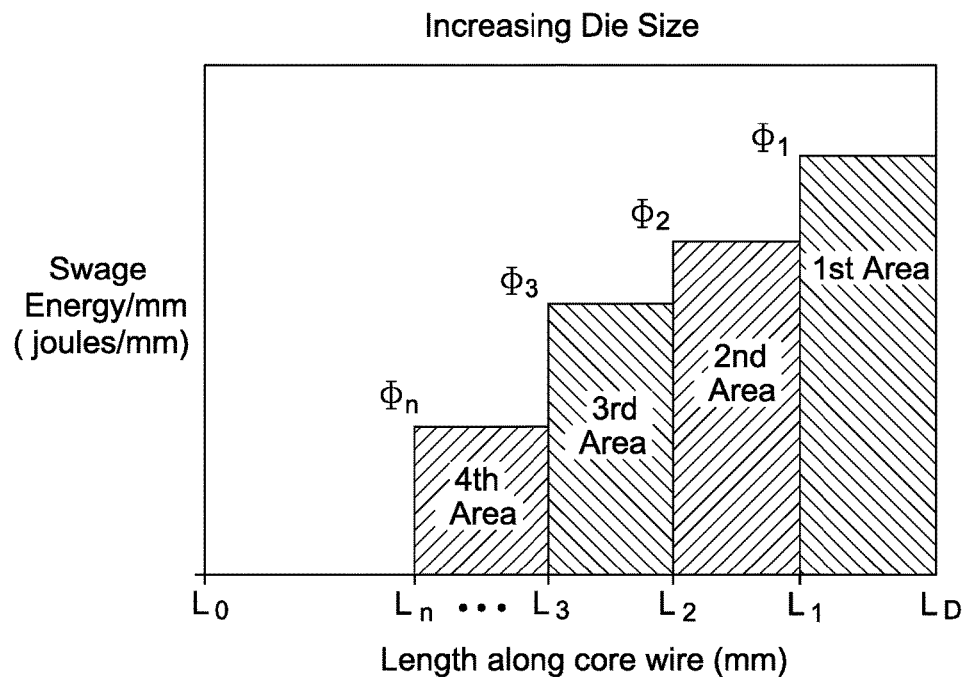
FIG. 18 is a schematic graph exemplifying how a method for fabricating a guidewire of a further embodiment is applied to a core wire.

FIG. 18 is a schematic graph clarifying by example how the technique of this embodiment is applied to a core wire. The horizontal axis of the graph reflects the length along a core wire from the proximal end, and the vertical axis reflects the cumulative amount of energy per unit length applied to the core wire through cold working by rotary swaging. As seen in FIG. 18, a rotary swager having a die set with diameter Φ1 is selected for first application of cold work. This diameter Φ1 will be the smallest diameter selected during the process of this embodiment. Starting at the very distal end of the core wire (the distal end at LD), the core wire is fed through the rotary swager so that cold work energy via rotary swaging is applied to core wire between LD and L1. As will be apparent to one of ordinary skill in the art, the area marked as "$1^{st}$ Area" on the graph schematically represents the amount of energy applied to the core wire by the dies having diameter Φ1, summed up over the length of the wire between LD and L1. Once the core wire is fed through the rotary swager up to L1, the die set is removed, and replaced with an alternative die set having an internal diameter Φ2, which is a diameter slightly larger than Φ1. Then, starting from a distance L1, the core wire is fed through the rotary swager so that cold work via rotary swaging is applied to core wire between L1 and L2. As will be apparent to one of ordinary skill in the art, the area marked as "$2^{nd}$ Area" on the graph schematically represents the amount of energy applied to the core wire by the die set having diameter Φ2, summed up over the length of the wire between L1 and L2. The process is continued, using increasingly larger dies, until an end point is reached, at Ln. The cumulative energy per unit length applied at any point to the core wire is reflected by the schematic graph in FIG. 18, with the greatest amount of energy per unit length applied at the distal end of the core wire. It will be understood that the profile of the wire will be stepped up (moving from distal to proximal end) at each point L1 through to Ln, and will resemble the structure exemplified in FIG. 11 at each stepping point. Finally, just as with the embodiment in FIG. 11, the core wire may be ground to desired profile using a grinding or reducing technique as described above. Thus, by a judicious selection of die sizes, and of starting points along the wire moving from distal to proximal ends, a core wire with desired stiffness at the distal end may be fabricated from a single strand of core wire.

Example 2

In applying the method of the embodiment described immediately above, the following parameters may be used to provide a core wire for a guidewire. These would provide a differentially cold worked tip suitable for receiving a bend for threading through the vasculature of a patient.

Core wire starting diameter=0.01750 inches (0.445 mm); Φ1=0.0148 inch (0.376 mm), L1 to LD=6 mm; Φ2=0.0152 inch (0.386 mm), L2 to LD=12 mm; Φ3=0.0156 inch (0.396 mm), L3 to LD=18 mm. Feed rate=0.217 mm/rev.; "n"=3.

Third Embodiment

Then, in a further embodiment, an approach may be applied in which only one die size is used. Under this method, repeat swaging strikes are performed on the distal most portion of the core wire, while fewer strikes are applied to the more proximal portion. This approach takes advantage of the redundant work inherent in rotary swaging by having the more distal sections undergo a greater die strike count. This results in greater overall cold work being performed on the distal portion, and thus greater shapeability at the distal core tip. The advantage of this approach is that, because only one die size is required, a more simplified manufacturing process may be achieved.

Figure 19:
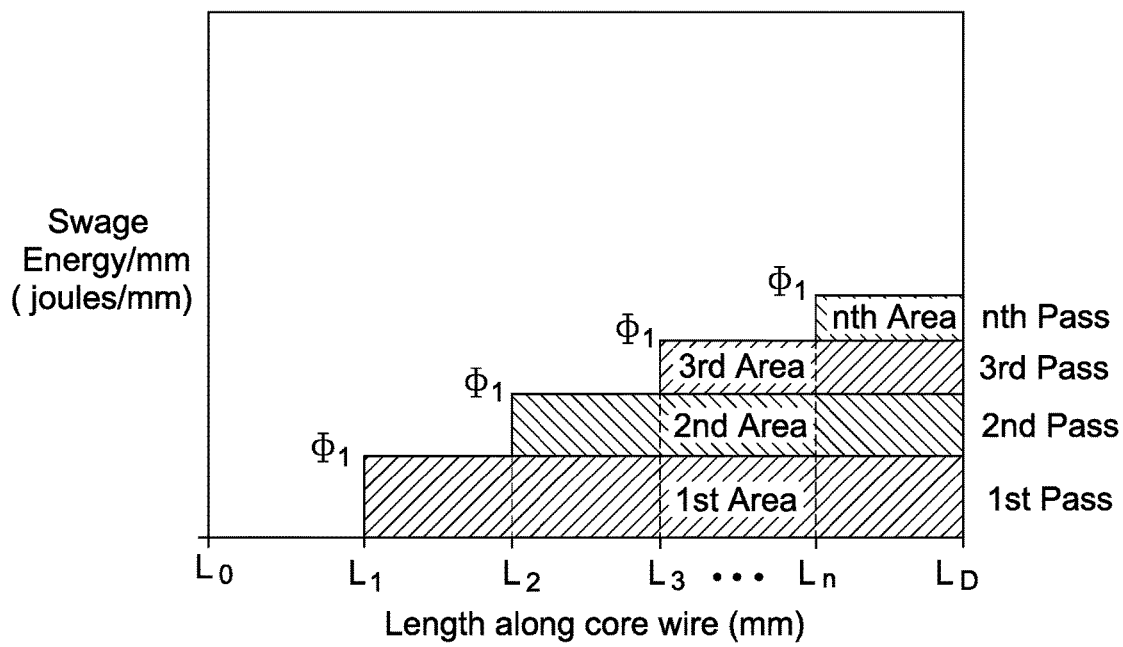
FIG. 19 is a schematic graph exemplifying how a method for fabricating a guidewire of yet a further embodiment is applied to a core wire.

FIG. 19 is a graph clarifying, by example, how the technique of this embodiment may be applied to a core wire. The horizontal axis of the graph reflects the length along a core wire from the proximal end, and the vertical axis reflects the cumulative amount of energy per unit length applied to the core wire through cold working by rotary swaging. As seen in FIG. 19, a rotary swager having a die set with diameter Φ1 is selected for first application of cold work. This diameter Φ1 will be the only diameter selected during the process of this embodiment. Starting at a length L1 from the distal end of the core wire (the proximal end starts at the origin, L0 and the distance from L0 to L1 may vary as needed), the core wire is fed through the rotary swager so that cold work energy via rotary swaging is applied to core wire between L1 and the distal end, LD. (Optionally, no cold work may be applied between L0 and L1, but in some embodiments, L1 may coincide with L0.) As will be apparent to one of ordinary skill in the art, the area marked as "$1^{st}$ Area" on the graph schematically represents the amount of energy applied to the core wire by the dies having diameter Φ1, summed up over the length of the wire between L1 and LD. Once the core wire is fed through the rotary swager, the wire is fed through the same set of dies once again. However, this time starting from a distance L2 from the distal end (L2 being further from the distal end than L1), the core wire is fed through the rotary swager so that cold work energy via rotary swaging is applied to core wire between L2 and the distal end, LD. As will be apparent to one of ordinary skill in the art, the area marked as "$2^{nd}$ Area" on the graph schematically represents the additional amount of energy applied to the core wire by the dies having diameter Φ1, summed up over the length of the wire between L2 and LD. As will be further apparent to one of ordinary skill in the art, the area falling within both "$1^{st}$ Area" and "$2^{nd}$ Area" now represents the cumulative energy applied by swaging under dies having diameter Φ1. Once the core is fed completely through the swager, a similar process may be followed starting at point L3 on the wire .

. . and then finally to starting point Ln. The cumulative energy per unit length applied at any point to the core wire is reflected by the graph in FIG. 19, with the greatest amount of energy per unit length applied at the distal end of the core wire. It will be understood that the profile of the wire will be stepped down at each point L1 through to Ln, and will resemble the structure exemplified in FIG. 11 at each stepping point. Finally, just as with the embodiment in FIG. 11, the core wire may be ground to profile using a grinding or reducing technique as described above. Thus, by a judicious selection of a single die size and of starting points along the wire, a core wire with desired stiffness at the distal end may be fabricated from a single strand of core wire.

Example 3

In applying the method of the embodiment described immediately above, the following parameters may be used to provide a core wire for a guidewire. These would provide a differentially cold worked tip suitable for receiving a bend for threading through the vasculature of a patient.

Core wire starting diameter=0.01750 inches (0.445 mm); $\Phi 1$=0.0148 inch (0.376 mm), L1 to LD=18 mm, passes=1; L2 to LD=12 mm, passes=2; L3 to LD=6 mm, passes=3. Feed rate=0.217 mm/rev for each pass; "n"=3.

Fourth Embodiment

Again, in yet a further embodiment, an approach is applied in which only one die size is used, but the feed rate by which the core wire is fed through the swager is varied along the overall length. In this embodiments, like in the previous embodiment, this approach takes advantage of the redundant work inherent in rotary swaging and results in greater die strike count and thus greater overall cold work, hence greater shapeability at the distal core tip. The advantage this approach the previous approach is that an equivalent result can be achieved in one pass at varying feed rate rather than performing multiple passes at a single feed rate as in the previous embodiment, thus further simplifying the manufacturing process.

Figure 20:
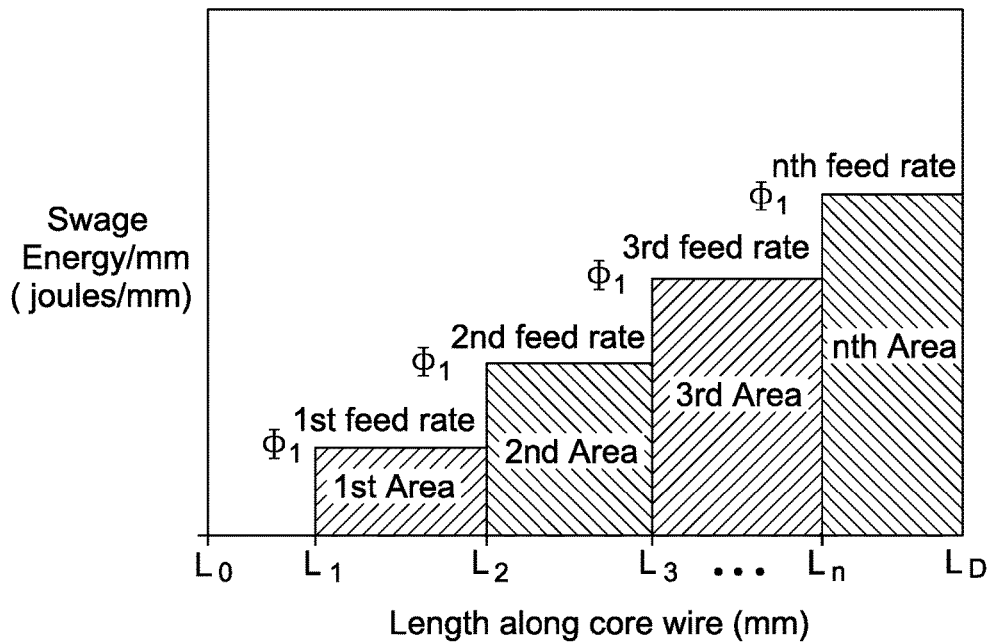
FIG. 20 is a schematic graph exemplifying how a method for fabricating a guidewire of yet another embodiment is applied to a core wire.

FIG. 20 is a graph clarifying by example how the technique of this embodiment may be applied to a core wire. The horizontal axis of the graph reflects the length along a core wire from the proximal end, and the vertical axis reflects the cumulative amount of energy per unit length applied to the core wire through cold working by rotary swaging. As seen in FIG. 20, a rotary swager having a die set with a diameter $\Phi 1$ is selected. No further die set with different diameter need be selected for use in the method of this embodiment. The core wire is inserted into the die set of the swager, and swaging is conducted at a point L1 along the wire, with the wire being fed into the swager so that the distal end LD of the wire moves up toward the dies at a constant rate. As the core wire moves into the swager so that the dies are positioned between L1 and L2, the feed rate is set at a First Feed Rate. When the wire reaches a point when the dies are located at L2, somewhat further from the proximal end, the feed rate is changed by slowing it down to a Second Feed Rate. It will be appreciated that slowing the feed rate has the effect of increasing the number of die strikes per unit length of core wire. This has the effect of increasing the amount of cold work imparted to the core wire over the length between L2 and L3, compared to over the length between L1 and L2. By corollary, when the wire reaches a point when the dies are located at L3, the feed rate is changed by slowing it down even further to a Third Feed Rate. This has the effect of increasing the amount of cold work imparted to the core wire over the length between L3 and Ln, compared to over the length between L2 and L3. The same process continues between the points Ln and LD at an nth Feed Rate, when the distal end of the wire reaches the dies. It will of course be understood that the same effect can be achieved, and falls within the scope of the invention, wherein the first length to be swaged is the portion between Ln and LD, thereafter proceeding proximally in a reverse sequence to that described above.

Example 4

In applying the method of the embodiment described immediately above, the following parameters may be used to provide a core wire for a guidewire. These would provide a differentially cold worked tip suitable for receiving a bend for threading through the vasculature of a patient.

Core wire starting diameter=0.01750 inches (0.445 mm); $\Phi 1$=0.0148 inch (0.376 mm); L1 to LD=18 mm, First Feed Rate=1.000 mm/rev; L2 to LD=12 mm, Second Feed Rate=0.500 rev/mm; L3 to LD=6 mm, Third Feed Rate=0.250 mm/rev.; "n"=3.

Thus, the embodiments described provide an advantageous system and method for manufacturing a medical guidewire core. The resulting guidewire has the advantageous feature of providing for a malleable distal tip, allowing a surgeon to fashion a shape selected to fit the problem confronted. Yet at the same time, the method of fabrication is simple, it requires no welding or joining techniques, and provides a wire that is not susceptible to cracking. The present invention may, of course, be carried out in other specific ways than those herein set forth without departing from the essential characteristics of the invention. The present embodiments are, therefore, to be considered in all respects as illustrative and not restrictive, while the scope of the invention is set forth in the claims that follow.

We claim:

1. A method of making a medical guidewire core element comprising:
    providing a wire of nickel titanium alloy with superelastic properties having a proximal end and a distal end, wherein a first length separates the proximal end from the distal end;
    applying cold work to the wire through a rotary swaging machine in a sequence that comprises:
        swaging the wire over a second length that includes the distal end by using a die set having a first diameter wherein the second length is less than the first length;
        swaging the wire over a third length that includes the distal end by using a die set having a second diameter, the third length being less than the second length, and the second diameter being less than the first diameter; and
    applying a reducing process to the wire, following swaging the wire over the second length and the third length, whereby the wire is reduced to have a constant diameter over the first length wherein the reducing process includes applying centerless grinding.

2. The method of claim 1, wherein wherein the second length is between 16 mm and 20 mm and the third length is between 10 mm and 14 mm.

3. The method of claim 1, wherein wherein the first diameter is between 0.356 mm and 0.436 mm and the second diameter is between 0.347 mm and 0.425 mm.

4. The method of claim 1, further including swaging the wire over a fourth length of the wire that includes the distal end by using a die set having a third diameter, wherein the fourth length is less than the third length and the third diameter is less than the second diameter.

5. A method of making a medical guidewire core element comprising:
- providing a wire of nickel titanium alloy with superelastic properties having a proximal end and a distal end, wherein a first length separates the proximal end from the distal end;
- applying cold work to the wire through a rotary swaging machine in a sequence that comprises:
  - swaging the wire over a second length between a first distal point and a first proximal point by using a die set having a first diameter;
  - swaging the wire over a third length between a second distal point and a second proximal point by using a die set having a second diameter, the second diameter being larger than the first diameter, further including selecting the second distal point to coincide with the first proximal point; and
  - applying a reducing process to the wire, following swaging the wire over the second length and the third length, whereby the wire is reduced to having a constant diameter over the first length wherein the reducing process includes applying centerless grinding.

6. The method of claim 5, wherein wherein the second length is between 4 mm and 8 mm and the third length is between 4 mm and 8 mm.

7. The method of claim 5, wherein the first diameter is between 0.338 mm and 0.414 mm and the second diameter is between 0.347 mm and 0.425 mm.

8. The method of claim 5, further including selecting the first distal point to coincide with the distal end.

9. The method of claim 5, further including swaging the wire over a fourth length of the wire between a third distal point and a third proximal point by using a die set having a third diameter, the third diameter being larger than the second diameter, and further including selecting the third distal point to coincide with the second proximal point.

* * * * *